United States Patent [19]

Birke

[11] Patent Number: 5,572,808
[45] Date of Patent: Nov. 12, 1996

[54] ORTHOPEDIC SHOE INSERT FOR CORRECTION OF THE ADDUCTION OF THE LARGE TOE

[75] Inventor: Josef Birke, Pirmasens/Pfalz, Germany

[73] Assignee: Solor Schuhforschung und Entwicklung-GmbH, Primasens/Pfalz, Germany

[21] Appl. No.: 890,612

[22] Filed: May 28, 1992

[30] Foreign Application Priority Data

May 31, 1991 [DE] Germany .............................. 9106735 U

[51] Int. Cl.⁶ .............................. A61F 5/14; A43B 13/38; A43B 23/00
[52] U.S. Cl. .................................. 36/140; 36/43
[58] Field of Search .................................. 36/68, 69, 71, 36/92, 94, 173, 174, 178, 43; 128/849, 882, 893

[56] References Cited

U.S. PATENT DOCUMENTS

| | | | |
|---|---|---|---|
| Re. 33,194 | 4/1990 | Marck et al. | 128/584 X |
| 2,423,622 | 7/1947 | Samblanet | 36/43 X |
| 4,813,159 | 3/1989 | Weiss | 36/43 |

FOREIGN PATENT DOCUMENTS

| | | |
|---|---|---|
| 130915 | 6/1984 | European Pat. Off. . |
| 2651469 | 5/1978 | Germany . |
| 2744445 | 1/1981 | Germany . |
| 3543642 | 6/1987 | Germany . |
| 9107481 | 9/1991 | Germany . |

Primary Examiner—B. Dayoan
Attorney, Agent, or Firm—Anderson, Kill, Olick P.C.

[57] ABSTRACT

An orthopedic shoe insert for correcting the adduction of the large toe is disclosed. The insert comprises generally a foot bed-like rear foot shell whose front edge lies approximately below the ball of the large toe and a corrective lobe molded on the side for supporting and guiding the large toe. The inside surface of the corrective lobe is slightly curved in a concave manner. Stiffening ribs are molded externally into the transition region between the corrective lobe and the rear foot shell. The lower edge of the corrective lobe is curved upwardly in order not to interfere with the rolling motion when walking. Because of the shaping and the use of elastic thermoplastic material, the corrective lobe is swiveled inwardly when walking, thereby actively correcting the malpositioning of the large toe.

8 Claims, 1 Drawing Sheet

ORTHOPEDIC SHOE INSERT FOR CORRECTION OF THE ADDUCTION OF THE LARGE TOE

FIELD OF THE INVENTION

The present invention is directed generally to shoe inserts and more specifically to individually fittable orthopedic shoe insert made of plastic material for correcting adduction defects of the large toe of the wearer.

BACKGROUND OF THE INVENTION

Mispositioning of the large toe so that it sticks out excessively (as with apes) is a mostly congenital abnormality. Special corrective inserts or insoles worn in orthopedic shoes may, in most cases, make it possible definitively to correct such adduction of the large toe. Such inserts are generally custom measured subsequent to consultation with a physician and typically consist of a foot bed-like rear foot shell which has a corrective lobe molded on the side adjacent to the large toe. The lobe is constructed such that the large toe is pressed into the desired direction toward the remaining toes. With progressive correctional success however, expensive new inserts are necessary since such correctional devices cannot be secured to this type of insert.

Apart from the shoe inserts, corrective rails are also employed for serious cases of adduction. In such cases, the devices are fastened to the leg and the foot. However these corrective rails cannot be worn in shoes. Another disadvantage of known corrective inserts is that the forwardly oriented corrective lobe easily breaks or lifts up the heel in the shoe because of the rolling motion when walking.

It is therefore an object of the invention to provide an orthopedic shoe insert for correction of adduction of the large toe wherein the corrective lobe is resistant to breakage.

Another object of the invention is to provide an orthopedic shoe insert for correction of adduction of the large toe wherein the corrective mechanisms are worn in the shoes.

SUMMARY OF THE INVENTION

These and other objects of the invention, which will be apparent hereafter, are achieved by the present orthopedic shoe insert for correction of adduction of a large toe. The insert is useable in a shoe and promotes a more rapid healing of the foot and can be readjusted according to the amount or degree of correction which has been accomplished. The device comprises generally an orthopedic shoe insert from plastic material having a foot bed-like rear foot shell whose front edge lies approximately beneath the ball of the large toe and an approximately vertically standing thermoplastic material corrective lobe supporting the large toe outwardly sideways, molded to the side of the shell. The corrective lobe is slightly inclined outwardly and its inside surface is slightly curved in a concave manner while its lower edge is curved in a convex manner.

The invention provides an inexpensive, light corrective insert which practically requires no space at all and can be worn in nearly all shoes, including shoes which are not orthopedic. The invention also contemplates active correction of the malpositioning, e.g. club foot, flat foot, pes valgus and pes cabu, of the rear parts of the feet.

BRIEF DESCRIPTION OF THE DRAWING

The invention will be better understood by the Detailed Description of the Preferred Embodiment, in connection with the drawing, of which.

DETAILED DESCRIPTION OF THE PREFERRED EMBODIMENT

Figures 1, 2:
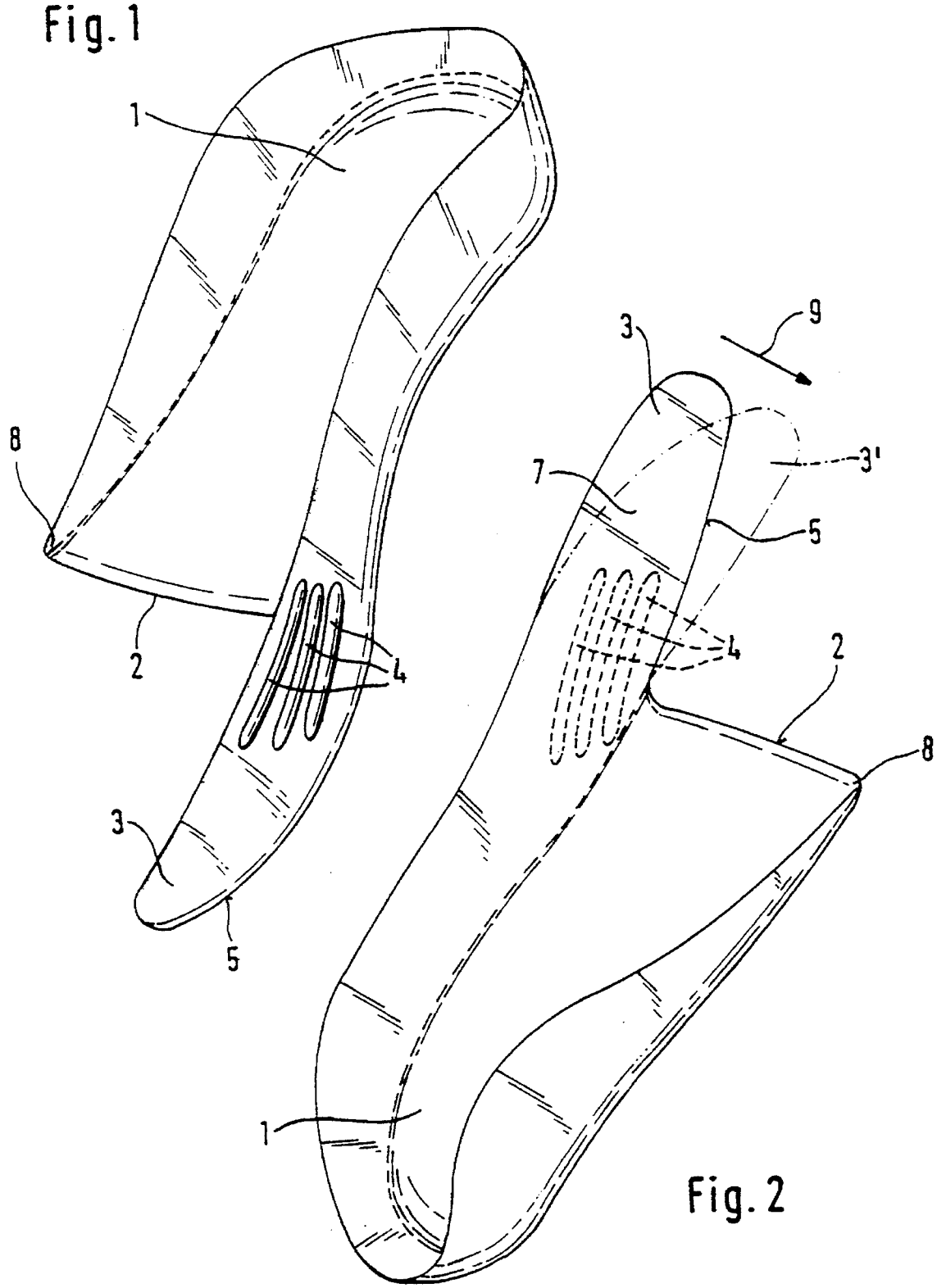
FIG. 1 is a perspective view of a corrective insert viewed obliquely from the front and the top.
FIG. 2 is another perspective view of the corrective insert of FIG. 1 viewed obliquely from the rear and the top.

Referring now to the figures, wherein like numerals depict like elements, FIGS. 1 and 2 depict an orthopedic shoe insert for correcting the adduction of the large toe, comprising a thermoplastic, elastic and preferably fracture-resistant material which can be mass-manufactured by the injection molding process. The material distribution can be optimally selected to correspond to various strength requirements. Because the shoe insert is manufactured from an elastic plastics material, the rolling motion of foot and shoe is not impeded when walking and is assisted by the bottom edge of the corrective lobe which is curved in a convex manner.

Because the insert is manufactured from thermoplastic plastics material, the blank fabricated in large quantities by the injection molding process can be easily fitted to the individual shape of the foot of even small size patients. The thermoplastic properties of the correction lobe facilitates its readjustment with progressive correctional success by heating of the plastics material.

The shoe insert comprises a foot bed-like rear foot shell 1 whose front edge 2 lies approximately below the ball of the large toe. A corrective lobe 3 is molded on the side of the rear foot shell 1 and is inclined outwardly at an angle of up to 15° with respect to the vertical plane. If the incline is more pronounced, the large toe could lose contact with the corrective lobe in spite of the concave, shell-like shape of its inner surface. The internal surface 7 of the lobe supporting the large toe is slightly concave, i.e., it is curved in a shell-like fashion so that the large toe is supported and guided, without being rigidly fixed.

Three stiffening ribs 4 are molded in the transitional region between the rear foot shell 1 and the corrective lobe 3, i.e, approximately in the region of the ball of the large toe. This helps prevent the corrective lobe 3 from swiveling outwardly by, for instance, the pressure of the large toe as well as by the dynamic processes of walking. The bottom edge 5 of the corrective lobe is curved upwardly in a convex manner and thus cannot interfere with the rolling motion when walking.

The corrective lobe 3 is swiveled outwardly by a specific angle during the rolling motion when walking because of the combined effect of the shell shape, slope or inclination and lower edge arching of the corrective lobe 3. (See FIG. 2, arrow 9.) The corrective lobe 3 attains the broken dotted position 3' and subsequently springs back again into its initial position especially under the pressure of the large toe. The large toe, which is resting against the lobe, is thus dynamically pressed with each step towards the desired parallel position, resulting in active correction of the toe.

Such active corrective motions of the corrective lobe 3 can be increased if the front edge 2 of the rear foot shell 1 from the tread of the ball towards the outer beam 8 is pulled slightly forward, i.e., by an angle of up to approximately 10°. Since the essentially stiff or rigid rear foot shell 1 tilts around the appropriately bent off edge 2 when walking, the corrective lobe 3 springs inwardly by a corresponding amount.

The front edge 2 in the rear foot shell proceeding from the corrective lobe is extended slightly forward, so that the external beam of the rear foot shell is longer than the tread of the ball of the foot. An angle of up to approximately 10° has been found to be optimum. During the rolling motion of the foot, the rear foot shell and the foot of the patient tilts around this slightly sloping front edge, whereby the corrective lobe and the large toe to be corrected flexes additionally in the right direction by an appropriate amount.

While the preferred embodiment of the invention has been described in detail, modifications and adaptations thereof may be undertaken with departing from the spirit and scope of the invention as delineated by the following claims:

What is claimed is:

1. An orthopedic shoe insert of plastic material for correcting the adduction of a large toe of a foot, comprising:
    a generally horizontal rear foot shell having a front edge lying approximately beneath a ball of the large toe, the ball having a tread;
    a rear edge and first and second side edges of the rear foot shell being integral with the bottom of a first portion of an approximately vertical wall;
    a second portion of the wall being integral with the first portion and extending forward beyond the front edge;
    the second portion being an approximately vertically standing thermoplastic material corrective lobe laterally supporting the large toe, wherein said corrective lobe is molded on a side of said rear foot shell for enabling lateral motion of the large toe, wherein the corrective lobe is inclined slightly; and
    said corrective lobe having a slightly curved concave inside surface and a lower edge convexly curved for enabling the unimpeded rolling motion of the foot during walking.

2. The shoe insert of claim 1, further comprising at least one stabilization rib molded in a transition region between the rear foot shell and the corrective lobe.

3. The shoe insert of claim 1, further comprising an external beam, wherein said front edge of the rear foot shell proceeding from the corrective lobe is pulled slightly forward so that said external beam is longer than the tread of the ball.

4. The insert shoe of claim 2, wherein said front edge of the rear foot shell proceeding from the corrective lobe is pulled slightly forward so that said external beam is longer than the tread of the ball.

5. The shoe insert of claim 3, wherein said front edge is pulled forward through an angle of approximately 10°.

6. The shoe insert of claim 4, wherein said front edge is pulled forward through an angle of approximately 10°.

7. The shoe insert as in any one of claims 1 to 5, wherein said corrective lobe is inclined laterally with respect to the vertical by approximately 5° to 15°.

8. The shoe insert as in any one of claims 1 to 5, wherein the plastic material is fracture resistant.

* * * * *